(12) United States Patent
Yang et al.

(10) Patent No.: US 11,333,661 B2
(45) Date of Patent: May 17, 2022

(54) DETECTION ANALYZER

(71) Applicants: CIXI INSTITUTE OF BIOMEDICAL ENGINEERING, NINGBO INSTITUTE OF INDUSTRIAL TECHNOLOGY, CHINESE ACADEMY OF SCIENCES, Cixi (CN); NINGBO INSTITUTE OF MATERIALS TECHNOLOGY & ENGINEERING, CHINESE ACADEMY OF SCIENCES, Ningbo (CN)

(72) Inventors: Fang Yang, Cixi (CN); Aiguo Wu, Cixi (CN)

(73) Assignees: CIXI INSTITUTE OF BIOMEDICAL ENGINEERING NINGBO INSTITUTE OF INDUSTRIAL TECHNOLOGY, CHINESE ACADEMY OF SCIENCES, Cixi (CN); NINGBO INSTITUTE OF MATERIALS TECHNOLOGY & ENGINEERING, CHINESE ACADEMY OF SCIENCES, Ningbo (CN)

( * ) Notice: Subject to any disclaimer, the term of this patent is extended or adjusted under 35 U.S.C. 154(b) by 417 days.

(21) Appl. No.: 16/486,587

(22) PCT Filed: Jan. 9, 2018

(86) PCT No.: PCT/CN2018/071835
§ 371 (c)(1),
(2) Date: Aug. 16, 2019

(87) PCT Pub. No.: WO2019/000902
PCT Pub. Date: Jan. 3, 2019

(65) Prior Publication Data
US 2020/0011853 A1    Jan. 9, 2020

(30) Foreign Application Priority Data

Jun. 28, 2017 (CN) .......................... 201710508203.5
Jun. 28, 2017 (CN) .......................... 201720764846.1

(51) Int. Cl.
G01N 33/50    (2006.01)
B01L 3/00     (2006.01)
G01N 33/15    (2006.01)

(52) U.S. Cl.
CPC .......... *G01N 33/5014* (2013.01); *B01L 3/508* (2013.01); *G01N 33/15* (2013.01);
(Continued)

(58) Field of Classification Search
CPC .............. G01N 33/5014; G01N 33/15; G01N 35/1095; G01N 33/48728; B01L 3/508;
(Continued)

(56) References Cited

U.S. PATENT DOCUMENTS 6,534,308 B1 *  3/2003  Palsson .................. C12M 35/02
                                                382/133
2002/0180315 A1 * 12/2002  Tanaka ................. H03H 9/1021
                                                310/348
(Continued)

FOREIGN PATENT DOCUMENTS

CN     2795853 Y     7/2006
CN     101346673 A   1/2009
(Continued)

OTHER PUBLICATIONS

Yang, Fang, et al. Real-time, label-free monitoring of cell viability based on cell adhesion measurements with an atomic force microscope. Journal of Nanobiotechnology. 2017, 10 pages, vol. 15, No. 23.
(Continued)

*Primary Examiner* — Benjamin R Whatley
*Assistant Examiner* — Jacqueline Brazin
(74) *Attorney, Agent, or Firm* — Maier & Maier, PLLC

(57) ABSTRACT

A detection analyzer including a first sample input/output element, a second sample input/output element, a sample compartment, a vibration platform, a vibration generator, a data acquisition system, a laser converter, and a data display. The first sample input/output element and the second sample input/output element are each connected to the sample compartment; the vibration platform is located inside the sample compartment; the vibration generator is located outside the sample compartment, and the vibration platform is connected to the vibration generator; the data acquisition system is located outside the sample compartment, and is connected to the vibration platform; and the data display is connected to the data acquisition system.

12 Claims, 4 Drawing Sheets

(52) U.S. Cl.
CPC ..... *B01L 2300/025* (2013.01); *B01L 2300/06* (2013.01); *B01L 2300/0645* (2013.01); *B01L 2300/12* (2013.01)

(58) Field of Classification Search
CPC ........... B01L 2300/025; B01L 2300/06; B01L 2300/0645; B01L 2300/12
USPC ...................................... 435/288.7
See application file for complete search history.

(56) References Cited

U.S. PATENT DOCUMENTS

| | | | |
|---|---|---|---|
| 2005/0199047 A1* | 9/2005 | Adams | G01Q 30/14 73/105 |
| 2007/0009982 A1* | 1/2007 | Thurlemann | G01N 33/4905 435/23 |
| 2008/0253641 A1 | 10/2008 | Ben-Shlomo et al. | |
| 2013/0059324 A1 | 3/2013 | Sittampalam et al. | |
| 2013/0156642 A1* | 6/2013 | Lous | G01N 21/645 422/52 |

FOREIGN PATENT DOCUMENTS

| | | |
|---|---|---|
| CN | 101373175 A | 2/2009 |
| CN | 101387636 A | 3/2009 |
| CN | 101514990 A | 8/2009 |
| CN | 102809597 A | 12/2012 |
| CN | 102914621 A | 2/2013 |
| CN | 103645347 A | 3/2014 |
| CN | 104965069 A | 10/2015 |
| CN | 105026936 A | 11/2015 |
| CN | 105181560 A | 12/2015 |
| CN | 105974145 A | 9/2016 |
| CN | 106687797 A | 5/2017 |
| DE | 621145 C | 11/1935 |

OTHER PUBLICATIONS

Cheimika. The KDS Legacy Series. Datasheet. Jun. 4, 2017. 8 pages. Italy.
International Search Report dated Mar. 28, 2018 in corresponding International Application No. PCT/CN2018/071835; 4 pages.
Chinese Office Action dated Dec. 18, 2019, in connection with corresponding CN Application No. 201710508203.5 (9 pgs., including machine-generated English translation).
Chinese Search Report dated Dec. 13, 2019, in connection with corresponding CN Application No. 201710508203.5 (5 pgs., including machine-generated English translation).
Second Chinese Office Action dated Apr. 3, 2020, in connection with corresponding CN Application No. 201710508203.5 (10 pp., including machine-generated English translation).
Chinese Search Repod dated Mar. 27, 2020, in connection with corresponding CN Application No. 201710508203.5 (4 pp., including machine-generated English translation).
Chinese Search Repod dated May 26, 2020, in connection with corresponding CN Application No. 201710508203.5 (3 pp., including machine-generated English translation).

* cited by examiner

DETECTION ANALYZER

TECHNICAL FIELD

The present application relates to a detection analyzer, and more particularly to an analyzer for multi-modal, dynamic biotoxicity real-time quantitative detection.

BACKGROUND

At present, the micro/nano electromechanical system is a popular technology, which is a frontier subject based on the micro/nano technology. Mechanical design, optical systems, drive elements, electronic control systems, and digital processing systems can be integrated into a single unit by designing, processing, manufacturing, and controlling micro/nano materials. Such a micro-electro-mechanical system is capable of not only collecting, processing and transmitting information or instructions, but also taking action autonomously or according to external commands in accordance with the acquired information. It is a manufacturing process that combines microelectronics and micromachining technology for manufacturing a wide range of high performance, low cost, miniaturized sensors, actuators, drivers and microsystems.

Different from traditional machinery, the machinery in the micro-electro-mechanical system represents all the effects with a function of energy conversion, including force, heat, sound, light, magnetism and even chemical biology. Therefore, the micro-electro-mechanical system involves in mechanical, electronic, chemical, physics, biology, materials and other disciplines. At the micrometer scale, the micromechanical structure still follows the traditional mechanical laws, but as the size reduced, the mass, heat capacity, etc. of the micromechanical device decrease, while the electrostatic force, resonance frequency, specific surface area, etc. increase. On the one hand, the performance such as the response time, sensitivity and working bandwidth of micromechanical devices, etc. can be improved using these size effects. On the other hand, these change regulation makes micromechanics susceptible to temperature, humidity and the like.

In addition, the mechanism of cellular dynamic poisoning has always been one of the core scientific issues that need to be solved in the field of biomedicine. After entering the 21st century, cytotoxicology has been developed slowly. In addition to the numerous indicators and complex evaluation factors, lacking of real-time, objective and accurate toxicity detection and analysis instruments is one of the important reasons that limit its development. In addition, the state has comprehensively monitored clinical drugs, and the safety and efficacy evaluation of drugs is one of its important auditing standards. However, there is no comprehensive, accurate and effective drug toxicity testing method currently. Therefore, real-time, continuous monitoring and analysis of the cytotoxic process through drug stimulation will provide a new approach to the investigation of cytotoxic mechanisms and the evaluation of new clinical drugs.

At present, most traditional cytotoxicity assays are usually based on time points. The dye marking method is used to evaluate the drug safety through subjective analysis of visualized cell morphology at different time periods. The reaction cycle is long, the dyeing process is cumbersome and the result is subjective. However, a minority of methods that can achieve dynamic toxicity detection cannot implement quantificational analysis due to the limitation of conditions, and are prone to side effects, thereby reducing the safety and accuracy of detection.

SUMMARY

In order to overcome the shortcomings of traditional biological toxicity detection methods, including: 1) a toxicity analysis method of time point type; 2) measurement result is visual picture analysis, subjectivity is strong; 3) high side effect on biological sample during measurement. In order to achieve continuous, long-term, real-time, quantitative, multi-mode dynamic monitoring, the present application has developed a multi-modal, dynamic biotoxicity real-time quantitative detection analyzer that utilizes a fixed-frequency vibration system to establish a vibration platform with adherent cells as the main test object. The analysis of the whole cell poisoning process is realized by utiliziing the intrinsic relationship between cell adhesion and cell state and real-time monitoring the electrical signal generated by the amplitude variation of the platform based on the mechanical polarization. The instrument will include four important elements, comprising: a vibration platform in a cellular environment, a dynamically balanced liquid retarder pump, an acquisition and analysis system for big data, and a multi-modal laser.

Accordingly, the present application provides a detection analyzer comprising a first sample input/output element, a second sample input/output element, a sample compartment, a vibration platform, a vibration generator, a data acquisition system, and a data display. Wherein the first sample input/output element and the second sample input/output element are respectively in communication with the sample compartment. The vibration platform is located in the sample compartment. The vibration generator is located outside the sample compartment and the vibration platform is connected to the vibration generator. The data acquisition system is located outside the sample compartment and is connected to the vibration platform; and the data display is connected to the data acquisition system.

Wherein, the sample compartment can maintain constant temperature and constant pressure according to the actual situation.

In a specific embodiment, the vibration platform is composed of a pressure sensitive material or a vibrating quartz material.

In a specific embodiment, the edge of the vibration platform is fixedly connected to the circuit board by an electronic element, and the circuit board is connected to an external vibration generator. Wherein, the electronic element can be selected from a conductor/semiconductor material. And the space between the vibration platform and the circuit board and between the electronic elements is tightly covered by an insulating material such as silicone/silicone oil.

In a specific embodiment, the vibration platform is a hollow structure, and the sample solution floods the vibration platform to bring the biological sample into contact with the vibration platform.

Wherein, the cavity portion around the vibration platform can be different from the material of the vibration platform.

Alternatively, in a specific embodiment, a portion of a side of the sample compartment that is in contact with the vibration platform is an inner recessed structure, so that it can be seamlessly inserted by the outer casing portion of the vibration platform. The outer casing is inserted into the recessed structure to achieve a good sealing performance, and the technical effect of preventing the sample liquid from overflowing from the sample compartment can be realized; the circuit board portion of the outer casing is convexly connected to the vibration generator.

Wherein, the sidewall of the recessed area of the sample compartment may be the same as the overall material of the sample compartment, or may be different from the material of the sample compartment; the material of the outer casing of the vibration platform may be the same as or different from the recessed area of the sample compartment.

In a specific embodiment, the data acquisition system includes a current collector and a data analysis module.

In a specific embodiment, the detection analyzer further includes a laser converter located below the sample compartment; a lower surface of the sample compartment is transparent.

In a specific embodiment, the detection analyzer further includes a driving device capable of simultaneously driving the first sample input/output element and the second sample input/output element such that a sample in the sample compartment is output to the second sample input/output element while the sample in the first sample input/output element is input to the sample compartment; or a sample in the sample compartment is output to the first sample input/output element while the sample in the second sample input/output element is input to the sample compartment.

In a specific embodiment, the first sample input/output element includes a first piston and a first reservoir, a first end of the first reservoir having a first opening, through which the first piston can enter a cavity of the first reservoir, a cavity of the first reservoir is close fitting with the first piston, and a second end of the first reservoir is connected to the sample compartment;

the second sample input/output element includes a second piston and a second reservoir, a first end of the second reservoir having a second opening through which the second piston can enter a cavity of the second reservoir, the cavity of the second reservoir is in close fitting with the second piston, and a second end of the second reservoir is connected to the sample compartment;

the driving device is disposed between the first piston that is exposed outside the cavity of the first reservoir and the second piston that is exposed outside the cavity of the second reservoir to drive the first piston and the second piston to move back and forth.

In a specific embodiment, the driving device includes a gear, a linkage further includes a motor that drives the rotation of the gear, and an electrode that controls the motor, the gear is capable of driving the first piston and the second piston to move back and forth, and the direction in which the first piston moves is opposite to the direction in which the second piston moves; a first gear reverse rotation switch capable of changing the rotation direction of the gear is provided at the first end of the first reservoir; a second gear reverse rotation switch capable of changing the rotation direction of the gear is provided at the first end of the second reservoir; and a first gear reverse rotation switch fitting member fitted with the first gear reverse rotation switch is disposed on the first piston, a second gear reverse rotation switch fitting member fitted with the second gear reverse rotation switch is disposed on the second piston; the electrode is controlled by the first gear reverse rotation switch or the second gear reverse rotation switch.

In a specific embodiment, the length of the first piston is at least 2 times the length of the cavity of the first reservoir; when one end of the first piston reaches the second end of the first reservoir, a portion exposed to the cavity of the first reservoir is a first outer piston;

the length of the second piston is at least 2 times the length of the cavity of the second reservoir; when one end of the second piston reaches the second end of the second reservoir, a portion exposed outside the cavity of the second reservoir is a second outer piston.

In a specific embodiment, the outer surface of the first outer piston is provided with a protrusion for increasing friction to fit with the gear; the outer surface of the second outer piston is provided with a protrusion for increasing friction to fit the gear.

In a specific embodiment, the contact surface of the first outer piston with the gear and the contact surface of the second outer piston with the gear each have a toothed structure that fits with the gear.

In a specific embodiment, the toothed structure protrudes from an outer surface of the first outer piston; and/or the toothed structure protrudes from an outer surface of the second outer piston.

In a specific embodiment, the toothed structure is recessed from the outer surface of the first outer piston; and/or the toothed structure is recessed from the outer surface of the second outer piston.

In a specific embodiment, when the first piston is in contact with the first gear reverse rotation switch, the toothed structure is located at an outer end of the first reservoir; when the second piston is in contact with the second gear reverse rotation switch, the toothed structure is located at an outer end of the second reservoir.

The beneficial effects that can be achieved by this application include:

1) The shape, surface area, material and size of the vibration platform of the present application may vary according to experimental requirements, that is, the vibration platform satisfies the requirements of a plurality of different types of cells to be detected.

2) The vibration platform of the present application is one-side two-way vibration, which can vibrate up and down or left and right, thereby reducing the vibration difference of each point on the vibration platform and ensuring the accuracy of the measurement; while some triangular vibration cantilever is one side vibration, the vibration generated by it is extremely uneven, and therefore, it is difficult to achieve an accurate degree of detecting the adhesion ability of cells by using this device.

3) In the present application, the data processing system is directly connected to the vibration platform, and there is no amplification processing problem of the data signal even if the mechanical signal is directly converted into an electrical signal, thus the data can be obtained directly and simply, also the deception of the data amplification is avoided; while the detection of some signals undergoes a process of amplifying a signal, which leading to the data cannot obtained directly on the one hand, and on the other hand, signal amplification tends to cause data distortion and the error becomes large.

4) In the present application, the system can perform real-time and quantitative analysis, which satisfies the requirements for timely processing and timely analysis, and avoids time waste; the existing device cannot realize real-time quantitative analysis.

5) In this application, by connecting with the laser converter, the instrument's detection function for materials can be expanded, and a new processing mode is opened and the requirements of real-time optical therapy can be met. For example, it is possible to detect the study of nano-particles with photodynamic therapy and photothermal therapy properties on cell treatment processes; the laser converters can also be applied to the study of optical on stem cell differentiation and functional transformation; the laser converters can also be applied to the study of the mechanism of effect of upconversion materials acting on cell.

6) The driving device of the present application realizes automation of sample input and output operations on the one hand, and is simple in structure and strong in operability on the other hand. A piezoelectric excitation-based resonant vibration platform biomass sensing system uses a vibration generator to bring the vibration platform to its resonant frequency, and then uses a two-way synchronous gear motor controlled sample input/output system to input samples, material or product solution to be tested into the sample compartment or output samples from the sample compartment at a constant and low speed to ensure the dynamic balance of the measurement condition in the sample compartment and the constant capacity of the sample. The noise impact on the vibration platform can be avoided by recording the small amplitude variation of the vibration platform for a long time and in real time using data acquisition system. In addition, the constant sample capacity also serves to prevent the sample from overflowing and damaging the instrument.

7) Using the detection analyzer of the present application, the cell-free label is realized, and no damage is caused to the cells, and the measurement result is objective and can truly reflect the biological toxicity of the sample to be tested; the resonant vibration platform sensing has high sensitivity characteristics and even if small amplitude changes can also be measured, the detection analyzer of the present application is accurate in quantitative detection, high in precision, and even can complete single cell detection and operation; a long-term, real-time, quantitative, continuous detection and analysis of amplitude changes instead of time-point analysis can be achieved.

DETAILED DESCRIPTION

The present application is described in detail below with reference to the examples, but the application is not limited to the examples.

Example 1 Detection Analyzer

Figure 1:
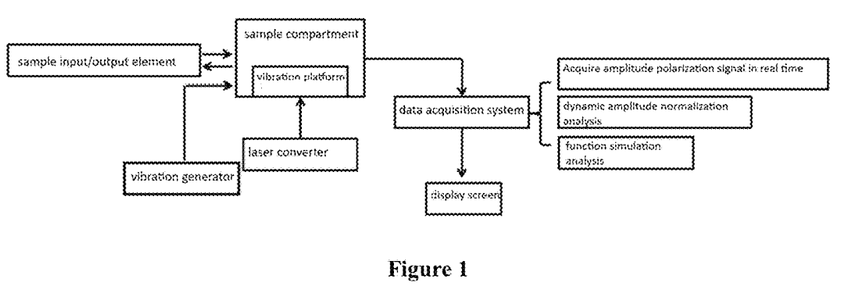
FIG. 1 shows a simplified workflow of a multimodal, dynamic biotoxicity real-time quantitative assay analyzer.

As shown in FIG. 1, it shows a simplified workflow diagram of a multimodal, dynamic biotoxicity real-time quantitative assay analyzer.

Wherein the vibration generator 1 has a function of driving the vibration platform 2 (piezoelectric crystal or oscillating quartz material) to vibrate at a fixed frequency by applying a voltage. The vibration generator 1 and the vibration platform 2 use a deep positive feedback crossover value in a multi-point contact manner to control the driving frequency by the twisting loop to satisfy the stress vibration mode of the low-error vibrator. The vibration generator 1 drives the vibration platform 2 to reach the resonance frequency. An amplitude of the vibration platform 2 being as low as 1 μV in the long-term and real-time test can also be collected by the data acquisition system 5 and data processed by processing software (for example, dynamic amplitude normalization software and function simulation software).

The vibration table 2 is driven by the driving frequency of the vibration generator 1 to vibrate at a fixed frequency. When a cell or biological tissue adheres to or falls off its surface due to the poisoning, external pressure acting on the surface causes a bending change of the vibrator, which further causes a corresponding polarization of the amplitude. Current collector (part of data acquisition system 5): acquiring amplitude polarization signal in real time and converting it to a filtered baseline, and signal resolution meeting 24 bit or more.

Data analysis module (a part of data acquisition system 5): normalizing the filtered baseline from the current collector while performing long-term and real-time raw data acquisition, and calculating the amplitude change after cell shedding or biological tissue variation (that is, the dynamic amplitude normalization analysis), and then simulating and analyzing decline coefficient by exponential function (see function simulation software interface 8 in FIG. 2), to achieve the purpose of quantitative analysis of biological toxicity and other characteristics. Wherein, the data acquisition system 5 first uses a dynamic amplitude normalization software and a function simulation software. Wherein, the function of the dynamic amplitude normalization software is to eliminate the baseline drift of amplitude, stabilize the baseline, that is, the baseline correction and eliminate the offset; the function of the function simulation software: when the data is analyzed later, the amount of amplitude change within a certain period of time can be calculated according to the demand. The dynamic amplitude normalization software and the function simulation software are available through conventional techniques in the art.

The equation for amplitude normalization uses a high-order polynomial, wherein f(t) is a function of instantaneous displacement and y is the displacement of the equilibrium position in the equation:

$$\sum_i (f(t_i) - y_i)^2 = \sum_i (a_n t_i^n + a_{n-1} t_i^{n-1} + \ldots + a_2 t_i^2 + a_1 t_i + a_0 - y_i)^2 = \text{Minimal}$$

The differential coefficient of the above polynomial sum is 0, and the amplitude balance point is normalized as shown in the following formula:

$$\frac{d}{da_s} \sum_i (a_n t_i^n + a_{n-1} t_i^{n-1} + a_{n-2} t_i^{n-2} + \ldots + a_2 t_i^2 + a_1 t_i a_0 - y_i)^2 = 0$$

$$a_n a_{n-1} \ldots a_1 a_0$$

$$\begin{pmatrix} \sum_i t_i^{2n} & \sum_i t_i^{2n-1} & \cdots & \sum_i t_i^{n+1} & \sum_i t_i^n & \bigg| & \sum_i y_i t_i^n \\ \sum_i t_i^{2n-1} & \sum_i t_i^{2n-2} & \cdots & \sum_i t_i^n & \sum_i t_i^{n-1} & \bigg| & \sum_i y_i t_i^{n-1} \\ \vdots & \vdots & \ddots & \vdots & \vdots & \bigg| & \vdots \\ \sum_i t_i^{n+1} & \sum_i t_i^n & \cdots & \sum_i t_i^2 & \sum_i t_i^1 & \bigg| & \sum_i y_i t_i^1 \\ \sum_i t_i^n & \sum_i t_i^{n-1} & \cdots & \sum_i t_i^1 & \sum_i t_i^0 & \bigg| & \sum_i y_i t_i^0 \end{pmatrix}$$

The function simulation program is based on the exponential function equation, A is the amplitude of the vibration platform 2, $A_0$ is the maximum amplitude of the vibration platform 2, B is the increment/decrement coefficient of the amplitude of the vibration platform 2, and t is the vibration time of the vibration platform 2, and the specific process of obtaining the B coefficient is as follows:

$$A(t) = A_0 e^{-Bt}$$

$$\ln A(t) = \ln A_0 - Bt$$

$$FQS(A_0, B) = \sum_{i=1}^{n}(\ln y_i - \ln A(t_i))^2 = \sum_{i=1}^{n}(\ln y_i - \ln A_0 + Bt_i)^2 = \text{minimal}$$

$$\frac{d}{dA_0} FQS(A_o, B) = -\left(\frac{2}{A_0}\right)\sum_{i=1}^{n}(\ln y_i - \ln A_0 + Bt_i)^n = 0$$

$$\frac{d}{dB} FQS(A_o, B) = 2\sum_{i=1}^{n} t_i(\ln y_i - \ln A_0 + Bt_i)^n = 0$$

$$A_0 = \exp\left(\frac{\sum_{i=1}^{n}\ln y_i \sum_{i=1}^{n} t_i^2 - \sum_{i=1}^{n} t_i \ln y_i \sum_{i=1}^{n} t_i}{n\sum_{i=1}^{n} t_i^2 - \left(\sum_{i=1}^{n} t_i\right)^2}\right)$$

$$B = \frac{n\ln A_0 - \sum_{i=1}^{n}\ln y_i}{\sum_{i=1}^{n} t_i}$$

Sample compartment 3: a vibration platform 2 is set therein, and a vertical and horizontal liquid input/output element 9, 9' controlled precisely by a motor is connected to a side wall thereof (see FIG. 4), for example the input/output element 9 can be controlled to a bidirectional flow rate of 10 μL/min without noise on the vibrator. Sample material can be input/output to the sample compartment 3 with this system. The flow rate of the inlet and outlet can be controlled by the system to keep consistent, so that the sample compartment 3 can be dynamically balanced, the volume of the fluid in the sample compartment 3 is kept constant, and the flow rate is small, so that the state of the vibration platform 2 is remained stable, and the noise caused by the change of sample amount on the vibration platform 2 is avoided. In addition, since the sample compartment 3 is required to satisfy the requirement of long-term observation of changes in live cytotoxicity, maintaining a constant biological environment is a necessary condition for its detection. For example, it is possible to heat and maintain a constant temperature of 37° C., and pass 5% $CO_2$ carbon dioxide to achieve environmental conditions for cell survival.

The laser converter 15 is located below the sample compartment 3 to meet the different wavelengths of excitation light required by different materials to generate photo-induced biochemical reactions, thereby causing corresponding changes in the organism to be tested. It can be used in research such as product photothermal/photodynamic therapy. The measured data is finally displayed on the display through a high-resolution data acquisition system.

Figure 2:
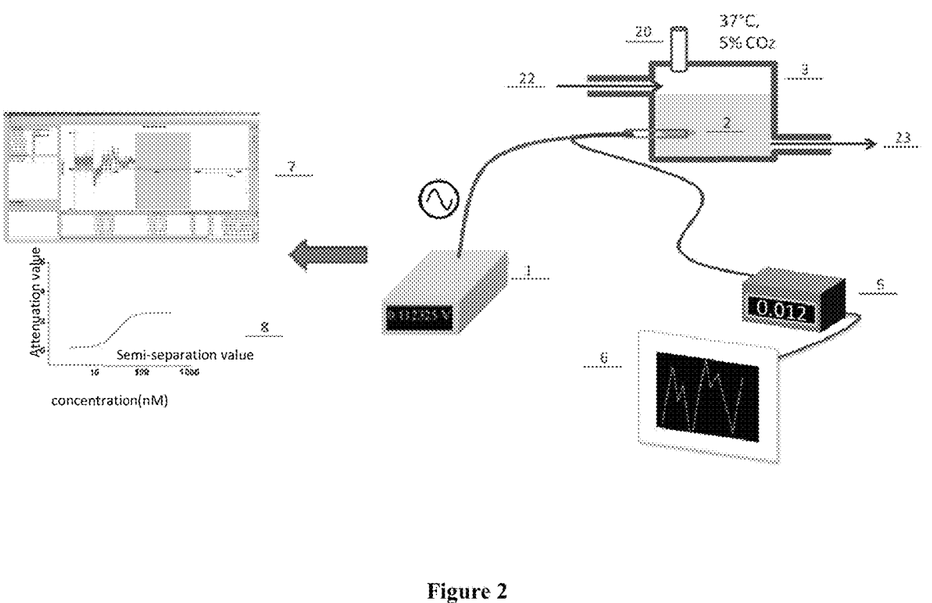
FIG. 2 shows an instrument and display interface diagram corresponding to the flow diagram of FIG. 1.

As shown in FIG. 2, an instrument and a display interface diagram corresponding to the flow diagram of FIG. 1 are shown. It comprises sample input/output elements 9, 9' (see FIG. 4), sample compartment 3, vibration platform 2, vibration generator 1, data acquisition system 5 and data display 6; wherein the sample input/output elements 9, 9' are communicating with the sample compartment 3; the vibration platform 2 is located in the sample compartment 3; the vibration generator 1 is located outside the sample compartment 3, and the vibration platform 2 is connected to the vibration generator 1;

the data acquisition system 5 is located outside the sample compartment 3 and is connected to the vibration platform 2; the data display 6 is connected to the data acquisition system 5.

Specifically, the edge of the vibration platform 2 extends downward to the lower surface of the sample compartment 3 to prevent the lower surface of the vibration platform 2 from contacting with the sample in the sample compartment 3.

Wherein, the portion of the vibration platform 2 that extends downward may be different from the material of the vibration platform 2.

Figure 3:
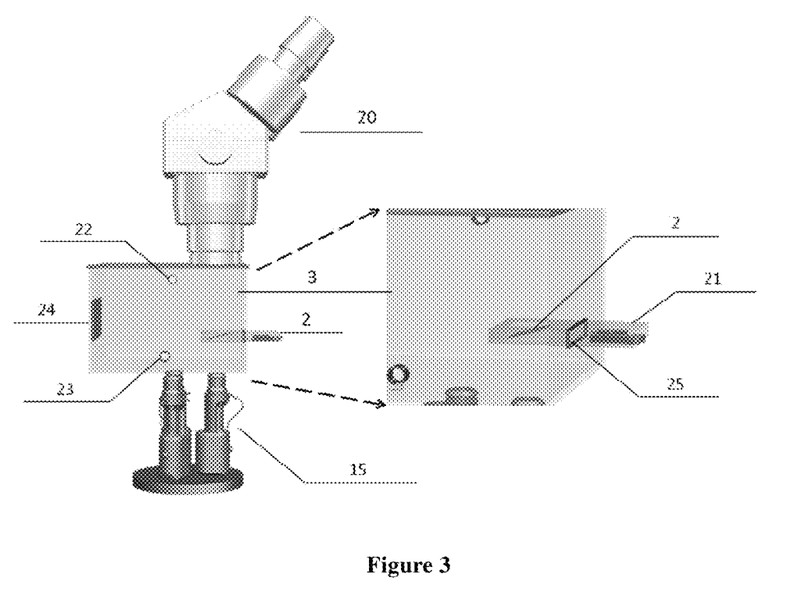
FIG. 3 shows the structure of the sample compartment, the vibration platform and the laser converter.

Alternatively, as shown in FIG. 3, the side surface area of the sample compartment 3 is recessed inwardly to form a recessed area, so that the outer casing portion of the vibration platform 2 is inserted into the opening of the recessed area, so that the vibration platform can be easily replaced. The outer casing is tightly sealed with the recessed area of the side wall to prevent the leakage of liquid. Wherein, the side wall of the recessed area of the sample compartment may be the same as the overall material of the sample compartment, or may be different from the material of the sample compartment. The material of the outer casing of the vibration platform may be the same as or different from the side wall of the recessed area of the sample compartment.

Further, the edge of the vibration platform 2 is fixedly connected to the circuit board 21 via the electronic element 25, and the circuit board 21 is connected to the external vibration generator 1. Wherein, the electronic element 25 can be selected from a conductor/semiconductor material. And the space between the vibration platform 2 and the circuit board 21 and the space between the electronic elements 25 are tightly covered by an insulating material such as silicone/silicone oil.

Figure 4:
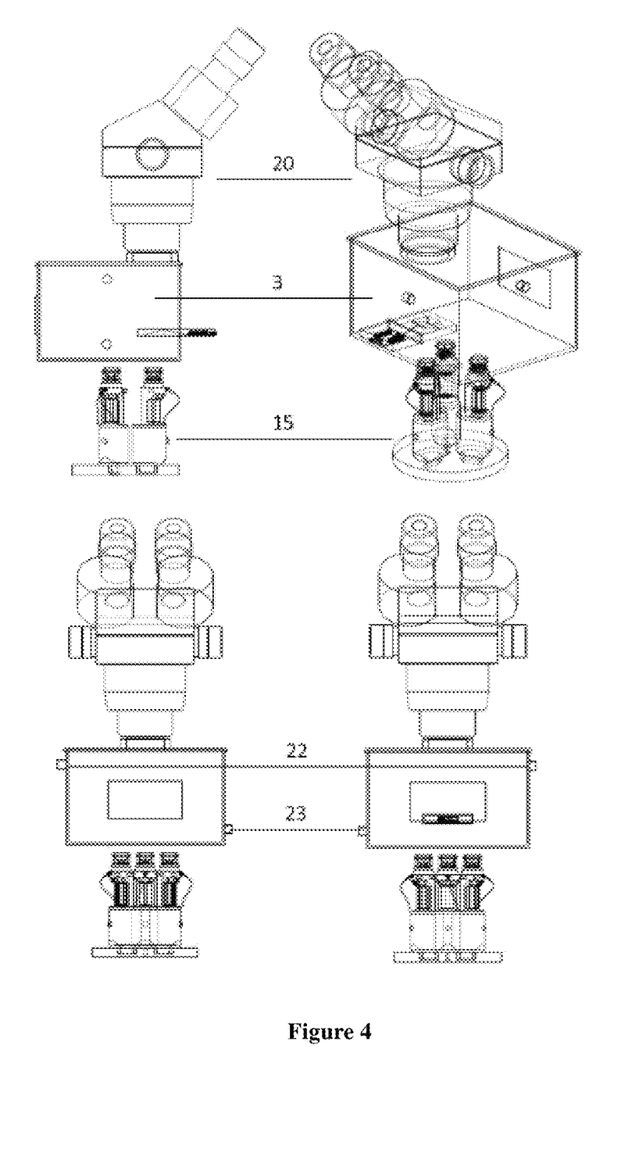
FIG. 4 shows a two-dimensional structure of the sample compartment, the vibration platform and the laser converter.

As shown in FIG. 4, the two-dimensional structure diagram of the sample compartment, the vibration platform and the laser converter is mainly shown. The top of the sample compartment 3 is connected to the optical microscope 20 to observe the biological sample on the vibration platform 2 conveniently; the side of the sample compartment 3 is connected to the vibration platform 2, and the outer casing of the vibration platform 2 is seamlessly connected with the recessed area of the sample compartment to prevent internal liquid from overflowing; the bottom of the sample compartment 3 is connected to the laser converter 15, and the bottom of the compartment is a transparent material, so that through which the laser light can be transmitted to act on the biological sample on the vibration platform; the liquid inlet 22 is located on the side of the sample compartment 3, and is higher than the vibration platform, and the liquid outlet 23 is located on the other side of the sample compartment 3 below the vibration platform while slightly above the bottom of the sample compartment 3 to facilitate cleaning of the sample compartment 3.

Figure 5:
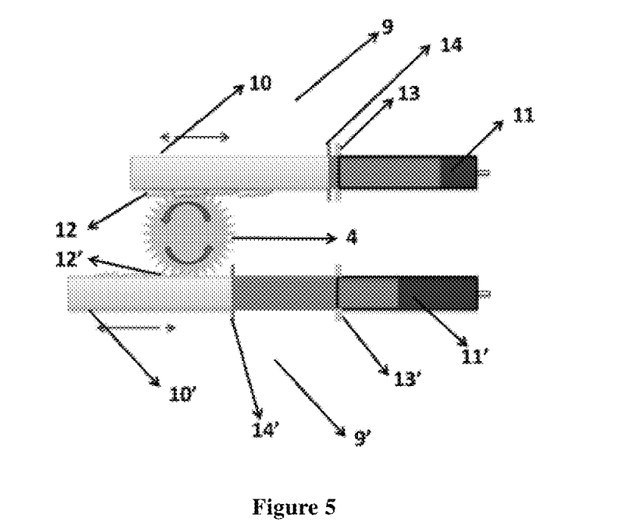
FIG. 5 shows a schematic of a linkage for the input and output of the sample.

As shown in FIG. 5, a schematic diagram of the linkage of the input and output of the sample is shown. The linkage of the input and output of the sample includes a first sample input/output element 9, a second sample input/output element 9', a sample compartment 3, and a driving device.

The first sample input/output element 9 includes a first piston 10 and a first reservoir 11, the first end of the first reservoir 11 having a first opening, through which the first piston 10 can enter a cavity of the first reservoir 11, the cavity of the first reservoir 11 is close fitting with the first piston 10, and a second end of the first reservoir 11 is connected to the sample compartment 3.

The second sample input/output element 9' includes a second piston 10' and a second reservoir 11', the first end of the second reservoir 11' having a second opening, through which the second piston 10' can enter a cavity of the second reservoir 11', the cavity of the second reservoir 11' is close fitting with the second piston 10', and a second end of the second reservoir 11' is connected to the sample compartment 3.

The driving device is disposed between the first piston 10 and the second piston 10' to drive the first piston 10 and the second piston 10' to move back and forth.

The driving device includes a gear 4, a linkage further includes a motor that drives the rotation of the gear, and an electrode that controls the motor, the gear 4 is capable of driving the first piston 10 and the second piston 10' to move back and forth, and the direction in which the first piston 10 moves is opposite to the direction in which the second piston 10' moves; a first gear reverse rotation switch 13 capable of changing the rotation direction of the gear 4 is provided at the first end of the first reservoir 11; a second gear reverse rotation switch 13' capable of changing the rotation direction of the gear 4 is provided at the first end of the second reservoir 11'; and a first gear reverse rotation switch fitting member 14 fitted with the first gear reverse rotation switch 13 is disposed on the first piston 10, a second gear reverse rotation switch fitting member 14' fitted with the second gear reverse rotation switch 13' is disposed on the second piston 10'; the electrode is controlled by the first gear reverse rotation switch 13 or the second gear reverse rotation switch 13'.

Specifically, the first gear reverse rotation switch 13 is disposed at the first opening and protrudes from the housing of the first reservoir 11; the second gear reverse rotation switch 13' is disposed at the second opening and protrudes from the housing of the second reservoir 11'. In addition, the first gear reverse rotation switch fitting member 14 is a protrusion protruding from the first piston 10, generally disposed in the middle of the first piston 10, or near the middle portion; the second gear reverse rotation switch fitting member 14' is a protrusion protruding from the second piston 10', generally disposed in the middle of the second piston 10', or near the middle portion. During the movement of the first piston 10 to the second end of the first reservoir 11, the first gear reverse rotation switch fitting member 14 will gradually approach the first gear reverse rotation switch 13 until it contacts the first gear reverse rotation switch 13, at this time a reversal rotation of the gear is triggered. Or during the movement of the second piston 10' to the second end of the second reservoir 11', the second gear reverse rotation switch fitting member 14' will gradually approach the second gear reverse rotation switch 13' until it contacts the second gear reverse rotation switch 13', at this time a reversal rotation of the gear is triggered. So reciprocating.

The contact surface of the first piston 10 and the gear 4 and the contact surface of the second piston 10' and the gear 4 each have toothed structures 12, 12' fitted with the gear 4;

The toothed structure 12 protrudes from the surface of the first piston 10; and/or the toothed structure 12' protrudes from the surface of the second piston 10'. In particular, it can be designed that the length of the first piston 10 is at least 2 times the length of the cavity of the first accumulator 11; when one end of the first piston 10 reaches the second end of the first accumulator 11, a portion of the first piston 10 exposed outside the cavity of the first accumulator 11 is a first outer piston, and a portion of the first piston 10 entering inside of the cavity of the first accumulator 11 is a first inner piston (in the figure, distinguishing from the first outer piston by the shades of color); at this time, the toothed structure 12 protrudes from the surface of the first outer piston. The length of the second piston 10' is at least 2 times the length of the cavity of the second accumulator 11'; when one end of the second piston 10' reaches the second end of the second accumulator 11', a portion of the second piston 10' exposed outside the cavity of the second accumulator 11' is a second outer piston, and a portion of the second piston 10' entering inside of the cavity of the second accumulator 11' is a second inner piston (in the figure, distinguishing from the second outer piston by the shades of color); at this time, the toothed structure 12' protrudes from the surface of the second outer piston.

Further, the toothed structure 12 may also be recessed from the surface of the first piston 10; the toothed structure 12' is recessed from the surface of the second piston 10'. In particular, it can be designed that the length of the first piston 10 is at least 2 times the length of the cavity of the first accumulator 11; when one end of the first piston 10 reaches the second end of the first accumulator 11, a portion of the first piston 10 exposed outside the cavity of the first accumulator 11 is a first outer piston, and a portion of the first piston 10 entering inside of the cavity of the first accumulator 11 is a first inner piston (in the figure, distinguishing from the first outer piston by the shades of color); at this time, the toothed structure 12 can also be recessed from the surface of the first outer piston. The length of the second piston 10' is at least 2 times the length of the cavity of the second accumulator 11'; when one end of the second piston 10' reaches the second end of the second accumulator 11', a portion of the second piston 10' exposed outside the cavity of the second accumulator 11' is a second outer piston, and a portion of the second piston 10' entering inside of the cavity of the second accumulator 11' is a second inner piston (in the figure, distinguishing from the second outer piston by the shades of color); at this time, the toothed structure 12' can also be recessed from the surface of the second outer piston.

The first gear reverse rotation switch fitting member 14 may also be disposed on the first inner piston, and at this time, the first gear reverse rotation switch fitting member 14 is disposed close to the position of the first outer piston; the second gear reverse rotation switch fitting member 14' may also be disposed on the second inner piston, and at this time, the second gear reverse rotation switch fitting member 14' is disposed close to the second outer piston.

Preferably, the first gear reverse rotation switch fitting member 14 is disposed at the intersection of the first outer piston and the first inner piston; the second gear reverse rotation switch fitting member 14' is disposed at the intersection of the second outer piston and the second inner piston.

Figure 6:
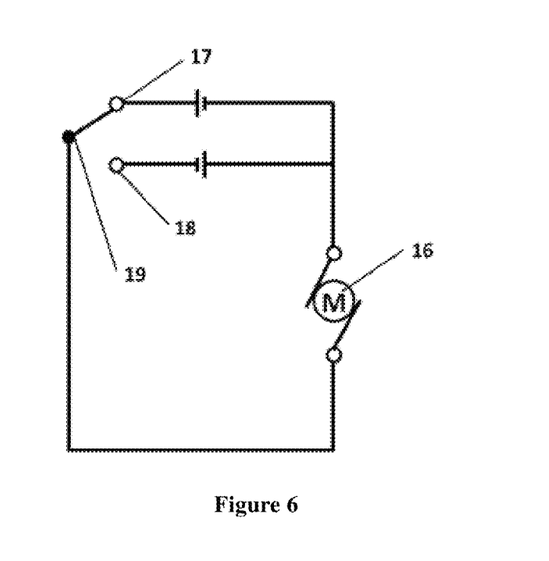
FIG. 6 shows a basic circuit diagram of the reverse rotation switch of the gear 4.

As shown in FIG. 6, it is a basic circuit diagram of the reverse rotation switch of the gear 4. Wherein 16 is a motor, when the first gear reverse rotation switch 13 is in contact with the first gear reverse rotation switch fitting member 14, the switch control member 19 is springed away from the first switch connecting member 17 and is in contact with the second switch connecting member 18; when the second gear reversing switch 13' is in contact with the second gear reverse rotation switch fitting member 14', the switch control member 19 is springed away from the second switch connecting member 18 and is in contact with the first switch connecting member 17.

The dynamic biotoxicity real-time quantitative detection analyzer can collect a raw data of at least 24 hours, and the resolution of the acquisition is high, and the changes in amplitude and waveform are finely visible, so that the subtle changes of the organism can be visually recognized real-time, and detected easily and quantitatively. In addition, cooperating the multi-modal laser to meet the requirements of multi-mode organism stress response, and detecting the biological toxicity change process of the material to be tested, thereby facilitating analysis of the toxicological type and mechanism of action of the material, which provides an effective experimental support for the study of biological toxicology and a new detection platform for the development of new drugs.

Example 2 Application

Preparation of Nanoparticles

Sodium citrate reduction method is used to synthesize gold nanoparticles commonly used in nanomedicine according to the method provided in the literature (Journal of Nanobiotechnology, 2017, 15(1): 23). The specific procedure is as follows: 144 ml of ultrapure water is added to a three-necked flask, heated to boiling, and then vigorously stirred after adding 3.5 ml of sodium citrate (60 mM) and 1.5 ml of citric acid (60 mM). 100 μl of EDTA is added and then 1 ml of chloroauric acid (25 mM) is added. When the color of the mixture turns into wine red, the heating is turned off, and it is immersed in ice water to stop the reaction when lowered to a certain temperature. Spherical gold nanoparticles with a particle size of 13 nm are synthesized.

The surface of the nano gold is coated with polyethylene glycol after the ligand exchange to improve the biocompatibility and stability of the nano particles.

Test the Maximum Uptake of Nanoparticles by Hela Cells

According to the method provided by the literature (Journal of Nanobiotechnology, 2017, 15(1): 23), this experiment is carried out on this dynamic biotoxicity real-time quantitative detection analyzer, and a certain concentration of Hela cells is input into/output from the sample compartment at a constant and slow speed of 10 μl/min through the sample input/output elements and the environment is maintained at 37° C. under constant conditions of 5% $CO_2$. When the observed amplitude is increased to a stable value, the number of cells attached to the vibration platform can be obtained through the amplitude change in the data display 6.

After that, a certain concentration of gold nanoparticles is slowly and constantly injected into the sample compartment, and the amplitude rising to a certain height for a certain period of time can be observed, and then the amplitude exhibits an exponential decay due to the cell poisoning. The maximum uptake of gold nanoparticles by Hela cells can be calculated by calculation. In addition, the mechanism of action of photodynamic therapy/photothermal therapy of nanoparticles can be quantitatively monitored and analyzed by the amount of dynamic amplitude attenuation.

The gold nanoparticles are replaced by NaGdF4:Yb/Tm@$TiO_2$ up-conversion particles, wherein $TiO_2$ is used as a photosensitizer. The multi-mode laser converter is converted to 980 nm after the up-converting nanoparticles are absorbed by the cancer cells, and the vibration platform is irradiated. The nanoparticles with photodynamic therapeutic effect will emit active oxygen to kill the cancer cells under the irradiation of the laser. This process is reflected in changes in amplitude and can be further analyzed based on this.

The above is only a few embodiments of the present application, and is not intended to limit the present application. The preferred embodiments are shown as above, but are not intended to limit the present application. A slight change or modification of the technical content disclosed above made by the person skilled in art without departing from the technical solution of the present application is equivalent to the equivalent embodiment, and is within the scope of the technical solution.

What is claimed is:

1. A detection analyzer, comprising:
   a first sample input/output element, a second sample input/output element, a sample compartment, a vibration platform, a vibration generator, a data acquisition system, a laser converter, and a data display; wherein the first sample input/output element and the second sample input/output element are respectively in communication with the sample compartment; the vibration platform is located in the sample compartment; the vibration generator is located outside the sample compartment and the vibration platform is connected to the vibration generator; the data acquisition system is located outside the sample compartment and is connected to the vibration platform; and the data display is connected to the data acquisition system;
   wherein the detection analyzer further comprises a driving device capable of simultaneously driving the first sample input/output element and the second sample input/output element, so that a sample in the sample compartment is output to the second sample input/output element while the sample in the first sample input/output element is input to the sample compartment; or
   a sample in the sample compartment is output to the first sample input/output element while the sample in the second sample input/output element is input to the sample compartment.

2. The detection analyzer according to claim 1, wherein the vibration platform is comprised of a pressure sensitive material or a vibrating quartz material.

3. The detection analyzer according to claim 1, wherein the edge of the vibration platform is fixedly connected to the circuit board by electronic elements, and the circuit board is connected to an external vibration generator.

4. The detection analyzer according to claim 1, wherein the vibration platform is a hollow structure.

5. The detection analyzer according to claim 1, wherein the portion of the side of the sample compartment contacting the vibration platform is an inner recessed structure, so that the outer casing portion of the vibration platform can be seamlessly inserted, and the outer casing of the vibration platform forms a sealing structure;

the portion of the circuit board in the outer casing of the vibration platform is convexly connected to the vibration generator.

6. The detection analyzer according to claim 1, wherein the data acquisition system comprises a current collector and a data analysis module.

7. The detection analyzer according to claim 1, wherein the laser converter is located below the sample compartment; the lower surface of the sample compartment is transparent.

8. The detection analyzer according to claim 1, wherein the first sample input/output element includes a first piston and a first reservoir, a first end of the first reservoir having a first opening, through which the first piston can enter a cavity of the first reservoir, the cavity of the first reservoir is close fitting with the first piston, and a second end of the first reservoir is connected to the sample compartment;

the second sample input/output element includes a second piston and a second reservoir, a first end of the second reservoir having a second opening through which the second piston can enter a cavity of the second reservoir, the cavity of the second reservoir is in close fitting with the second piston, and a second end of the second reservoir is connected to the sample compartment; and the driving device is disposed between the first piston that is exposed outside the cavity of the first reservoir and the second piston that is exposed outside the cavity of the second reservoir to drive the first piston and the second piston to move back and forth.

9. The detection analyzer according to claim 8, wherein the driving device includes a gear, a linkage further includes a motor that drives the rotation of the gear, and an electrode that controls the motor, the gear is capable of driving the first piston and the second piston to move back and forth, and the direction in which the first piston moves is opposite to the direction in which the second piston moves; a first gear reverse rotation switch capable of changing the rotation direction of the gear is provided at the first end of the first reservoir; a second gear reverse rotation switch capable of changing the rotation direction of the gear is provided at the first end of the second reservoir; and a first gear reverse rotation switch fitting member fitted with the first gear reverse rotation switch is disposed on the first piston, a second gear reverse rotation switch fitting member fitted with the second gear reverse rotation switch is disposed on the second piston; the electrode is controlled by the first gear reverse rotation switch or the second gear reverse rotation switch.

10. The detection analyzer according to claim 9, wherein the length of the first piston is at least twice the length of the cavity of the first reservoir; when one end of the first piston reaches the second end of the first reservoir, a portion exposed outside the cavity of the first reservoir is a first outer piston; and the length of the second piston is at least twice the length of the cavity of the second reservoir; when one end of the second piston reaches the second end of the second reservoir, a portion exposed outside the cavity of the second reservoir is a second outer piston.

11. The detection analyzer according to claim 10, wherein the outer surface of the first outer piston is provided with a protrusion for increasing friction to fit with the gear; the outer surface of the second outer piston is provided with a protrusion for increasing friction to fit the gear; or the contact surface of the first outer piston with the gear and the contact surface of the second outer piston with the gear each have a toothed structure that fits with the gear.

12. The detection analyzer according to claim 10, wherein the toothed structure protrudes from an outer surface of the first outer piston; and/or the toothed structure protrudes from an outer surface of the second outer piston; or the toothed structure is recessed from the outer surface of the first outer piston; and/or the toothed structure is recessed from the outer surface of the second outer piston.

* * * * *